(12) United States Patent
Sheldon

(10) Patent No.: US 7,819,522 B2
(45) Date of Patent: Oct. 26, 2010

(54) FLEXIBLE EYEWEAR FRAME WITH RIGID LENS RETAINER

(76) Inventor: Brent Sheldon, 72 Sherbrooke West, Suite #3, Montreal, QC (CA) H2X 1X3

(*) Notice: Subject to any disclaimer, the term of this patent is extended or adjusted under 35 U.S.C. 154(b) by 58 days.

(21) Appl. No.: 12/392,447

(22) Filed: Feb. 25, 2009

(65) Prior Publication Data

US 2010/0214528 A1 Aug. 26, 2010

(51) Int. Cl.
G02C 1/00 (2006.01)
G02C 1/04 (2006.01)
(52) U.S. Cl. .......................... 351/86; 351/85; 351/106; 351/178
(58) Field of Classification Search .................... 351/86, 351/85, 106, 83, 103, 154, 92, 93, 95, 96, 351/41, 178
See application file for complete search history.

(56) References Cited

U.S. PATENT DOCUMENTS

| | | | |
|---|---|---|---|
| 3,838,914 A * | 10/1974 | Fernandez | 351/106 |
| 4,196,982 A * | 4/1980 | Watkins | 351/86 |
| 6,517,202 B2 * | 2/2003 | Huang | 351/103 |
| 6,601,954 B2 * | 8/2003 | Menon | 351/86 |
| 6,896,365 B1 * | 5/2005 | Lin | 351/62 |
| 6,899,427 B1 | 5/2005 | Sheldon | |
| 6,959,988 B1 | 11/2005 | Sheldon | |
| 6,971,745 B2 | 12/2005 | Sheldon | |
| 7,316,479 B1 | 1/2008 | Matera | |
| 7,325,919 B2 | 2/2008 | Sheldon | |
| 2005/0036101 A1 | 2/2005 | Actis-Datta | |
| 2005/0073643 A1 | 4/2005 | Sheldon | |
| 2005/0254001 A1 | 11/2005 | Winningham | |
| 2006/0050227 A1 | 3/2006 | Fernandez et al. | |
| 2007/0132944 A1 | 6/2007 | Sheldon | |

OTHER PUBLICATIONS

International Search Report mailed on May 19, 2010, on Applicant's corresponding PCT International Patent Application No. PCT/CA2010/000156.

* cited by examiner

*Primary Examiner*—Hung X Dang
(74) *Attorney, Agent, or Firm*—Ogilvy Renault LLP

(57) ABSTRACT

A rigid lens retaining apparatus is permanently engaged with a substantially flexible eyewear frame during a formation molding process of the frame to provide a secure and releasable attachment of lenses to the substantially flexible eyewear frame through the rigid lens retaining apparatus.

15 Claims, 6 Drawing Sheets

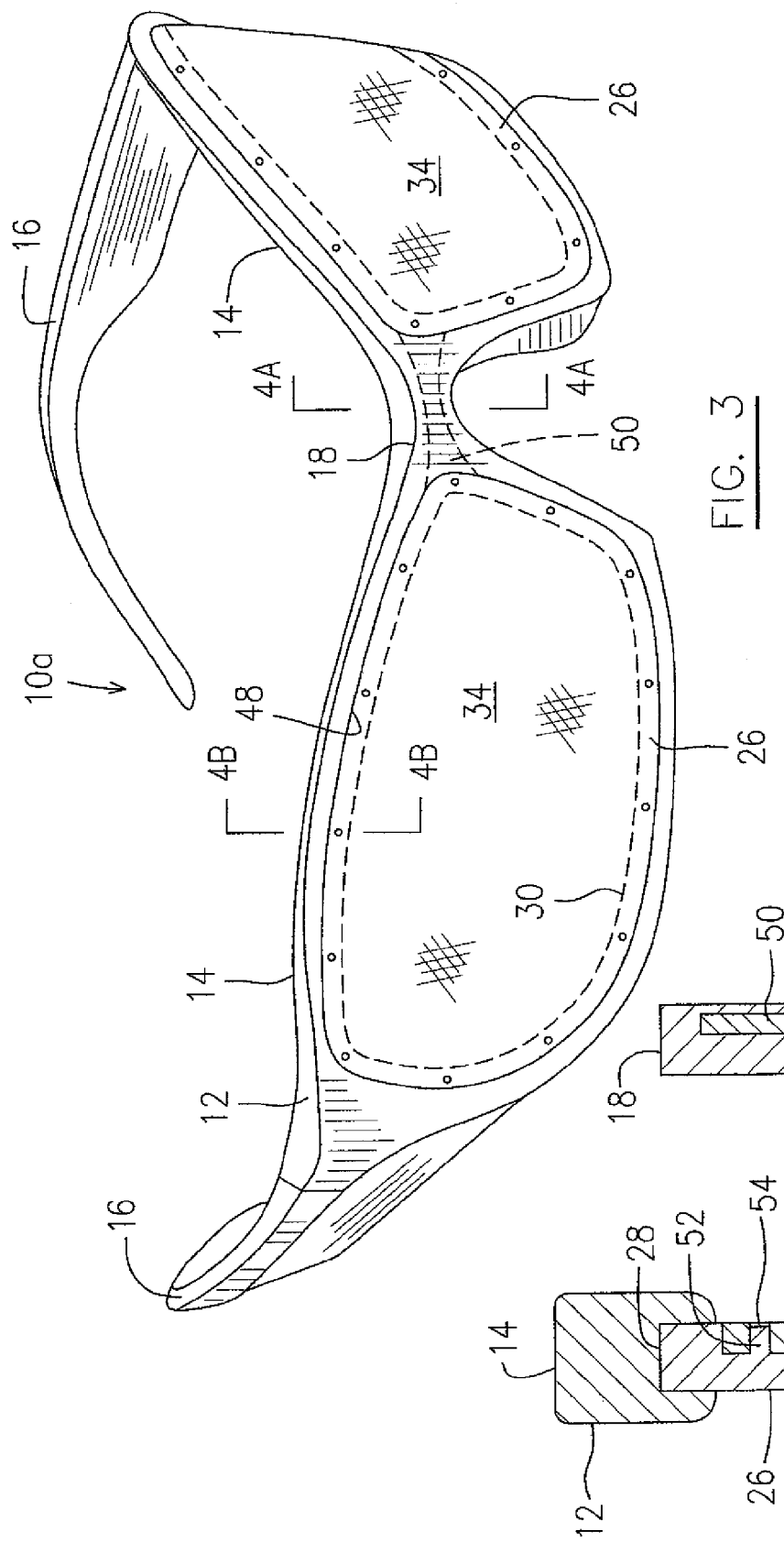

FLEXIBLE EYEWEAR FRAME WITH RIGID LENS RETAINER

TECHNICAL FIELD

The present invention relates to eyewear, and more particularly to eyewear having a substantially flexible frame with a rigid lens retaining apparatus for releasably securing one or more lenses to the eyewear frame.

BACKGROUND OF THE INVENTION

Conventional eyewear generally includes an eyewear frame with a head support apparatus and one or more lenses attached to the frame. For example, the eyewear frame may be made of substantially rigid plastic material and configured to define one or two lens openings for releasably engaging one or two lenses with the rigid frame. These eyewear include a variety of eyeglasses, such as sunglasses, protective work glasses, sports goggles, etc.

There is a demand for more variety of eyewear to satisfy new functional requirements and new fashions. Therefore, there is a need for eyewear having substantially flexible eyewear frames in different types of eyeglasses or goggles, in which lenses may be conveniently attached to and detached from the eyewear structure. However, it is a challenge to securely but releasably engage lenses to a substantially flexible eyewear frame, particularly when the substantially flexible frame does not completely encircle the attached lenses. Accordingly, improved eyewear is needed to solve this problem.

SUMMARY OF THE INVENTION

In accordance with one aspect of the present invention, there is a method provided for making eye glasses comprising steps in a following sequence: (a) providing a molding device for molding a substantially flexible glasses frame; (b) placing at least one rigid lens retainer in a predetermined position with respect to the molding device to permit a portion of the molding device to overlap a first portion of the rigid lens retainer; (c) forming the substantially flexible glasses frame with permanent engagement of the rigid lens retainer thereto, in a molding process using the molding device; and then (d) releasably engaging at least one lens with the rigid lens retainer to have the lens be in direct contact with a second portion of the rigid lens retainer.

In accordance with another aspect of the present invention, there is provided eye glasses which comprise a substantially flexible molded glasses frame; a rigid lens retaining apparatus including first and second portions thereof, the first portion being permanently engaged with a portion of the substantially flexible molded glasses frame during a molding formation of the frame with the presence of the rigid lens retaining apparatus; and at least one lens in direct contact and releasably engaged with the second portion of the rigid lens retaining apparatus.

Other features and advantages of the present invention will be better understood with reference to the preferred embodiments described hereinafter.

BRIEF DESCRIPTION OF THE DRAWINGS

Having thus generally described the nature of the present invention, reference will now be made to the accompanying drawings, showing by way of illustration the preferred embodiments thereof in which:

FIG. 3 is a perspective view of eyewear according to another embodiment of the present invention;

FIG. 4A is partial cross-sectional view of the eyewear of FIG. 3 taken along line 4A-4A, showing a connection portion embedded in the eyewear frame to interconnect two rigid lens retainers;

FIG. 4B is a partial cross-sectional view of the eyewear of FIG. 3 taken along line 4B-4B, showing a structural arrangement thereof;

DETAILED DESCRIPTION OF THE PREFERRED EMBODIMENT

Figure 1:
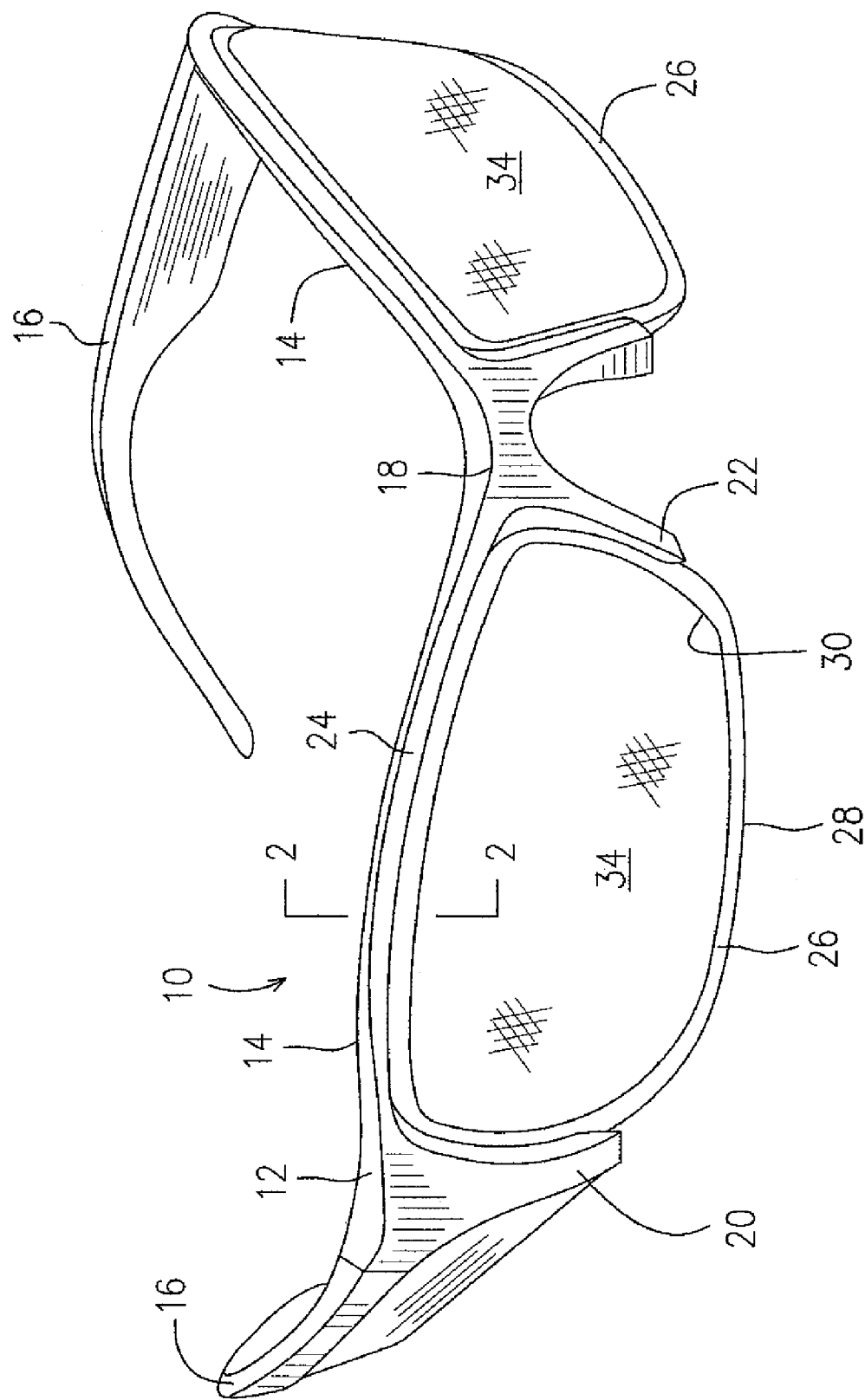
FIG. 1 is a perspective view incorporating one embodiment of the present invention.
Figure 2A:
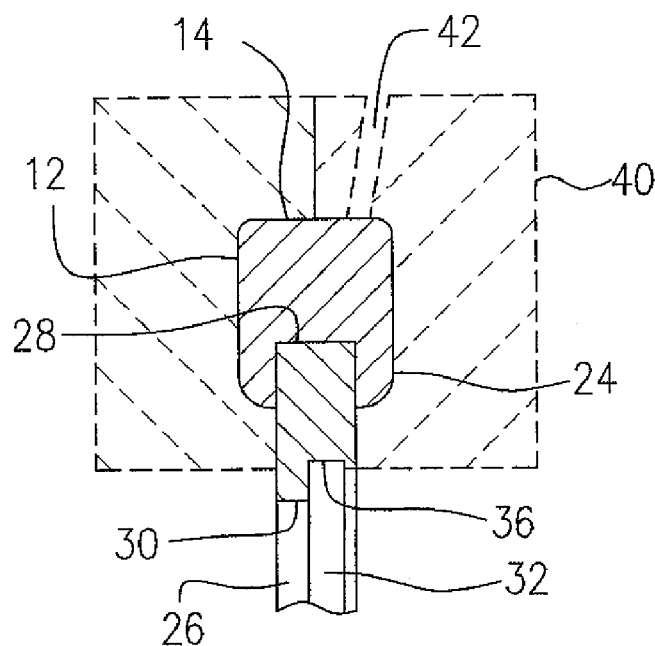
FIG. 2A is a partial cross-sectional view of a substantially flexible frame of the eyewear of FIG. 1 in a molding formation process with the presence of a rigid lens retainer.

Referring to FIGS. 1-2A, eyewear 10 includes a substantially flexible eyewear frame 12 such that the frame structure can be somewhat elastically deformed without damage. The substantially flexible eyewear frame 12 in accordance with one embodiment generally includes a pair of lens support sections 14 interconnected by a nose bridge 18. The substantially flexible eyewear frame 12 is integrally made with a suitable molding material in a formation molding process. Each of the lens support sections 14 has outer and inner side portions 20, 22 spaced apart one from another and extending downwardly from an upper portion 24 of the respective lens support sections 14. A head support means such as a pair of arms 16 are, for example, pivotally attached to opposite ends of the eyewear frame 12, and may be made of similar molding material and possess similar flexible properties.

A rigid lens retaining apparatus which includes two rigid lens retainers 26 according to this embodiment, is permanently engaged with the substantially flexible eyewear frame 12 during a formation molding process of the eyewear frame 12, with the presence of the rigid lens retaining apparatus.

Each of the rigid lens retainers 26 is made, for example of a substantially rigid plastic material in a manufacturing process separate from the formation molding process of the substantially flexible eyewear frame 12. For ease of discussion only one lens retainer will be discussed hereinafter. The lens retainer 26 has a continuous outer periphery 28. An upper section of the outer periphery 28 is in direct contact with the eyewear frame 12, and more particularly, is received and permanently engaged with a reversed U-shaped profile which is formed in combination with the outer and inner side portions 20, 22 and upper portion 24 of the lens support section 14. The rigid lens retainer 26 also includes a continuous inner periphery 30 which defines a lens opening 32 (see FIG. 2A) for receiving a lens 34 therein. The rigid lens retainer 26 therefore encircles the lens 34.

Removable engagement of the lens 34 to the rigid lens retainer 26 is achieved, for example by a shallow groove 36 provided along the inner periphery 30 of the rigid lens retainer 26 which is configured to allow the outer periphery of the lens 34 to be engaged in the shallow groove 36 in a "click-in" action when the lens 34 is pressed into the lens opening 36 from one side of the rigid lens retainer 26. The lens 34 can be conveniently removed from the lens retainer 26 in a "click-out" action when the lens 34 is pressed from the other side of the lens retainer 26. Alternatively, the lens can be removably attached to the rigid lens retainer using other mechanisms based on elastic displacement deformation of or frictional forces between the lens and the rigid lens retainer, particularly when the rigid lens retainer is configured differently, such as defining a non-encircling configuration which engages only part of the periphery of the lens. It should be noted that the attachment of the lens to the rigid lens retainer is completed after the lens retainer 26 is permanently engaged with the substantially flexible eyewear frame 12, in order to avoid subjecting the lens 34 to the conditions of the formation molding process of the eyewear frame.

Particularly referring to FIG. 2A, a molding device 40 defines a cavity (not numbered) in accordance with the configuration of the substantially flexible eyewear frame 12. The molding device 40 further includes a molding injection passage 42 communicating with the cavity in order to permit injection of the molding material in an appropriate state, into the cavity during the formation molding process. The respective rigid lens retainers 26 are placed in first and second predetermined positions with respect to the molding device 40. A portion of the molding device overlaps a part of the outer peripheral portion of the lens retainers 26 at both sides thereof such that a part of the outer peripheral portion of the respective rigid lens retainer 26 is embedded by the molding material of the substantially flexible eyewear frame 12. When the molding material of the eyewear frame 12 is cured, the lens retainers 26 are permanently engaged with the substantially flexible eyewear frame 12.

Figure 2B:
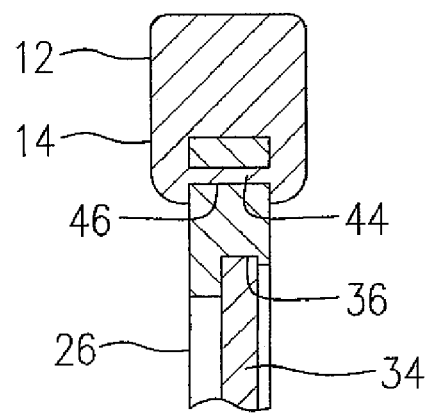
FIG. 2B is a partial cross-sectional view of the eyewear of FIG. 1 taken along line 2-2, showing a structural arrangement alternative to that shown in FIG. 2A.
Figure 2C:
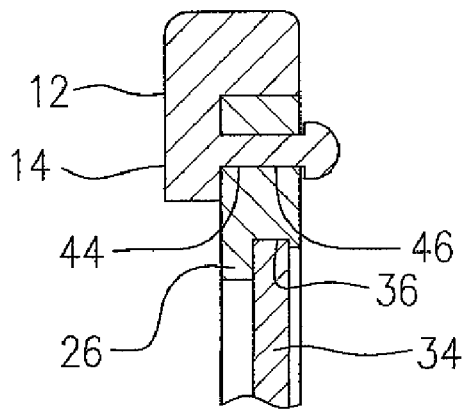
FIG. 2C is a partial cross-sectional view of the eyewear of FIG. 1 similar to the view of FIG. 2B, showing another alternative structural arrangement.
Figure 2D:
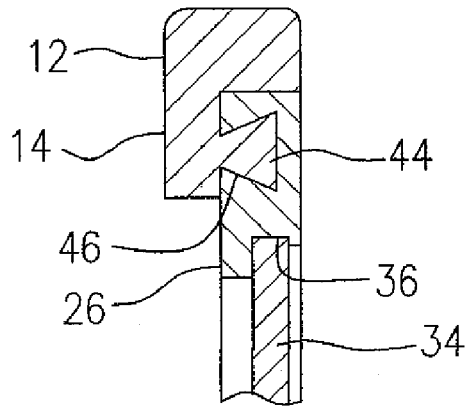
FIG. 2D is a partial cross-sectional view of the eyewear of FIG. 1 similar to the view of FIG. 2B, showing a further alternative structural arrangement.

FIGS. 2C and 2D illustrate an alternative structural arrangement of the permanent engagement of the rigid lens retainer 26 with the substantially flexible eyewear frame 12, which is achieved by allowing a portion of a molding material of the substantially flexible eyewear frame 12 to flow into one or more cavities 46 defined in a peripheral portion of the rigid lens retainer 26, thereby forming one or more projecting elements 44 of the flexible eyewear frame 26 to be engaged within the one or more cavities 46 of the lens retainers 26, when the molding material is cured. The projecting elements 44 may be configured in various shapes, such as having an enlarged dimension at a distal end of the projecting element 44, in order to prevent withdrawal of the projecting elements 44 from the cavities 46. The lens 34 is releasably engaged with the groove 36 of the rigid lens retainer 26.

FIG. 2B shows a further alternative structural arrangement in which a peripheral portion of the rigid lens retainer 26 is embedded in the substantially flexible eyewear frame 12 while a portion of a molding material of the substantially flexible eyewear frame 12 is introduced into one or more cavities 46 (or openings) in the rigid lens retainer 26, during a formation molding process of the substantially flexible eyewear frame 12, in order to form the one or more projecting elements 44 (or studs) engaged in the one or more cavities 46 (or openings).

In FIGS. 3, 4A and 4B, eyewear 10a according to another embodiment, is illustrated and includes similar parts indicated by similar reference numerals with respect to eyewear 10 of FIG. 1. The description of eyewear 10a will be focused on the structural differences between eyewear 10a and eyewear 10 of FIG. 1. The substantially flexible eyewear frame 12 of eyewear 10a, similar to eyewear 10 of FIG. 1, also includes a pair of lens support sections 14 interconnected by a nose bridge 18, and is provided with pivotal arms 16. However, each of the lens support sections 14 is configured to have a continuous inner peripheral edge 48 which defines an opening (not numbered).

Each of the rigid lens retainers 26, similar to that of eyewear 10 of FIG. 1, includes the continuous outer and inner peripheral edges 28, 30 (see FIG. 4B). It should be noted that the rigid lens retainer 26 is configured to substantially match but be slightly larger than the contour of the opening defined by the continuous inner peripheral edge 48 of the lens support section 14. Therefore, an entire portion of the rigid lens retainer 26 along its circumferential periphery is embedded in the substantially flexible eyewear frame 12 during a formation molding process of the frame 12 using a method similar to that described above with regard to formation of eyewear 10 of FIG. 1. As part of the lens retaining apparatus, a connection portion 50 is provided to connect the pair of rigid lens retainers 26 and may be made of a similar or different material. The connection portion 50 may be provided integrally with or separately from the rigid lens retainers 26 during manufacturing. The connection portion 50 is also embedded in the eyewear frame 12, for example by being completely covered by the material forming the nose bridge 18 of the eyewear frame 12 (see FIG. 4A)

The rigid lens retainer 26 further includes a plurality of projecting elements, for example, studs 52 extending substantially parallel one to another and projecting outwardly from the rigid lens retainer 26. Studs 52 are frictionally engaged in respective openings 54 defined along a peripheral portion of the lens 34, such that the lens 34 is releasably engaged with the rigid lens retainer 26 after the lens retainer is permanently attached to the substantially flexible eyewear frame 12.

Figure 5A:
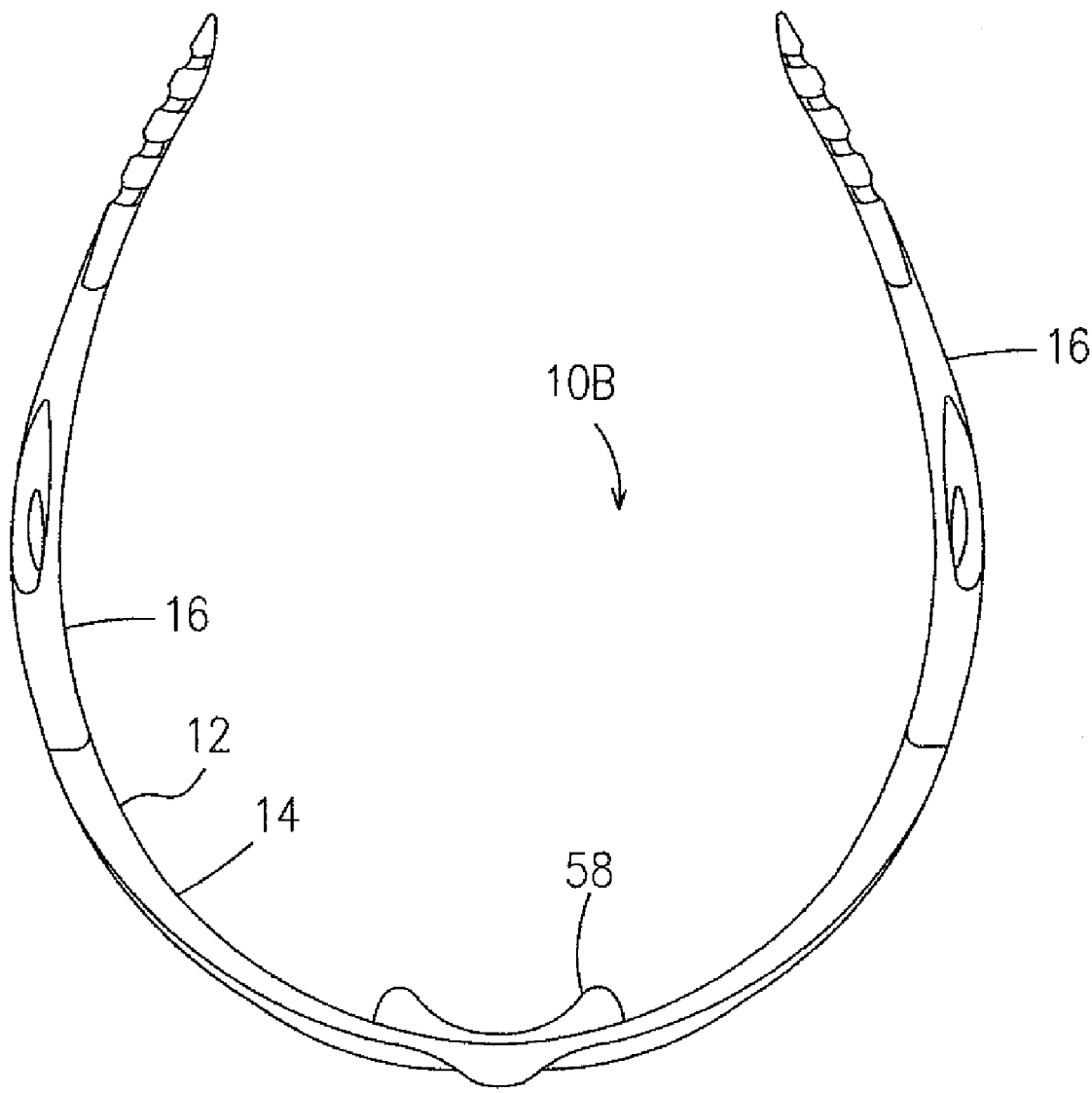
FIG. 5A is a top plan view of eyewear according to another embodiment of the present invention.
Figure 5B:
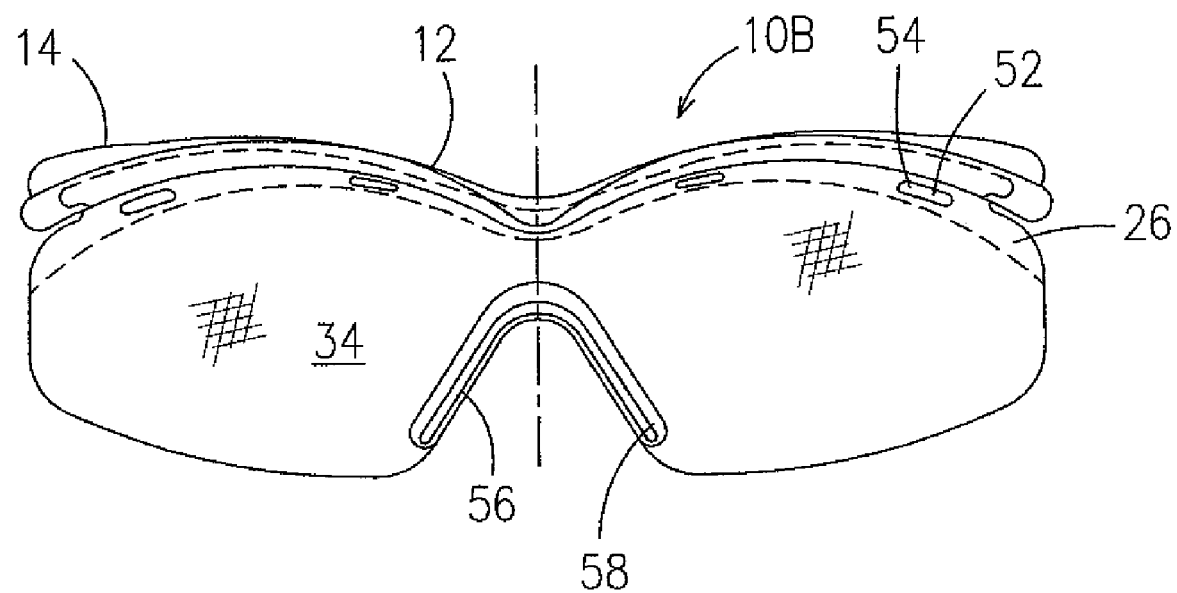
FIG. 5B is a front elevational view of the eyewear of FIG. 5A, with two arms removed.

In FIGS. 5A and 5B, eyewear 10b according to another embodiment of the present invention, generally includes similar components and features indicated by similar reference numerals with respect to the eyewear 10 of FIG. 1. The description of eyewear 10b will be focused on the structural differences between eyewear 10b and eyewear 10 of FIG. 1. Eyewear 10b includes a substantially flexible eyewear frame 12 which is made in a formation molding process similar to that of eyewear 10 of FIG. 1. The eyewear frame 10b includes an elongate base which forms a lens support section 14. The elongate base preferably has a curvature so as to fit with a user's face and a pair of arms 16 pivotally attached to opposed ends of the elongate base, respectively. A single rigid lens retainer 26 which forms the lens retaining apparatus, is permanently attached to the lens support section 14 of the eyewear frame 12 for detachably securing a single lens 34.

A top portion of the single rigid lens retainer 26 is embedded in a bottom portion of the substantially flexible eyewear frame 12 during a formation molding process, similar to that described above with reference to FIG. 2A. Therefore, the permanent engagement of the single rigid lens retainer 26 to the lens support section 14 of the substantially flexible eyewear frame 12 is achieved after the molding material of the eyewear frame 12 is cured. Various structural arrangements such as shown in FIGS. 2A to 2D may be selected for the permanent arrangement of the single rigid lens retainer 26 to the lens support section 14 of eyewear 10B.

In this embodiment the single rigid lens retainer 26 includes one or more projecting elements 52 which are configured in an elongate profile to correspond with the aesthetics of the elongate base of the eyewear frame 12. The projecting elements 52 are frictionally engaged in one or more elongated openings defined in the single lens 34 along a top edge thereof, similar to the releasable engagement of the lens 34 to the inner periphery 30 of the lens retainer 26 of eyewear 10a as shown in FIG. 4b.

The single lens 34 preferably defines a nose recess 56 at a centre of a bottom periphery thereof. A nose support member 58 is positioned at the nose recess 56 and is attached to the single lens 34 by well known means.

Figure 6:
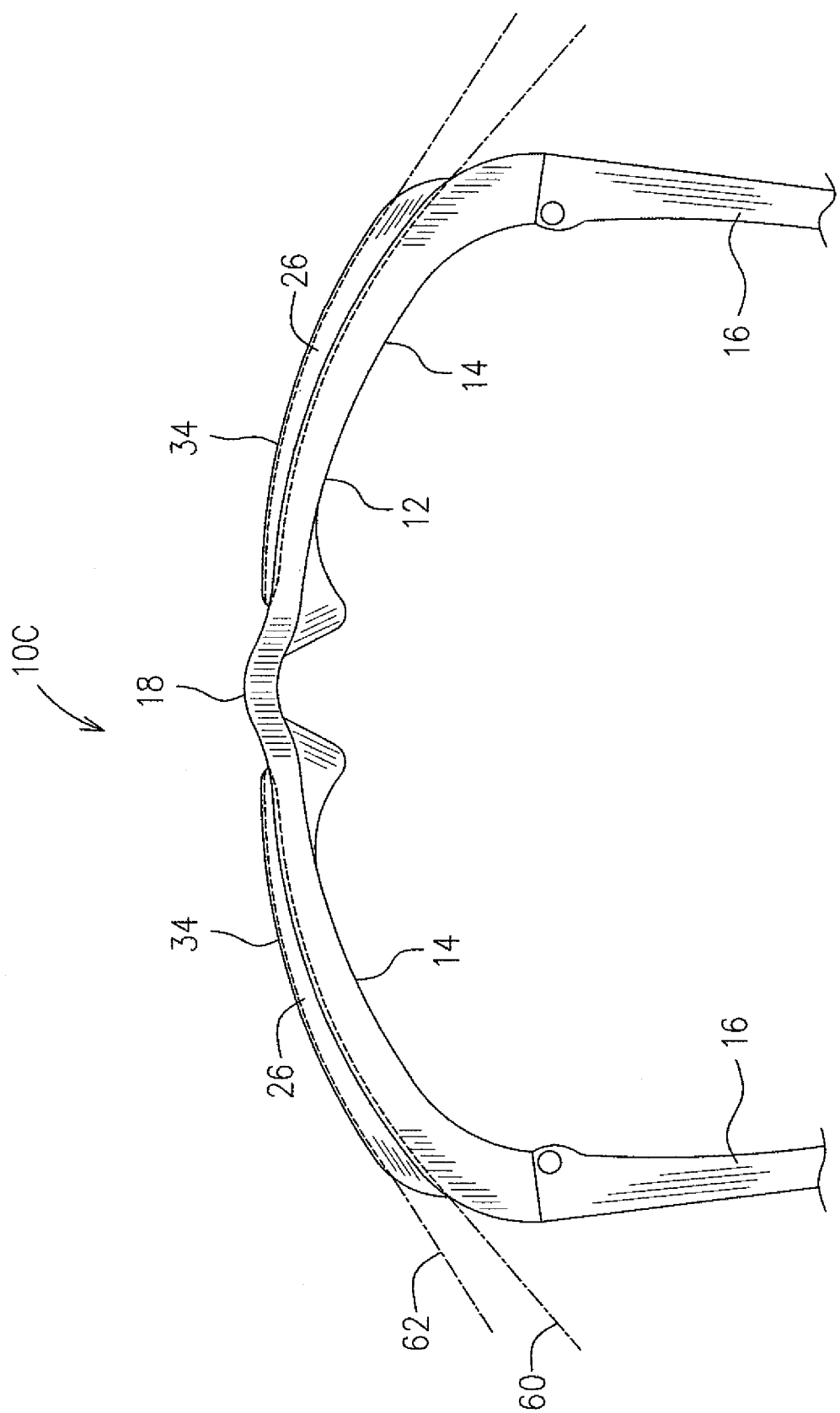
FIG. 6 is a top plan view of eyewear according to a further embodiment of the present invention, showing a curved profile of rigid lens retainers to match respective curvatures of the lenses and the eyewear frame.

In FIG. 6, eyewear 10c according to a still further embodiment of the present invention, includes similar components and features indicated by similar reference numerals with respect to eyewear 10 of FIG. 1. The description of eyewear 10c will be focused on the structural differences between eyewear 10c and eyewear 10 of FIG. 1. A substantially flexible eyewear frame 12 of eyewear 10c, is provided at the opposed ends thereof with a pair of arms 16 pivotally attached thereto. The substantially flexible eyewear frame 12 has a pair of lens support sections 14 interconnected by a nose bridge 18 to support and permanently engage a pair of rigid lens retainers 26. Each of the rigid lens retainers 26 which may be configured in any shape such as used in eyewear 10, 10a and 10b shown in FIGS. 1-5B, defines a curved profile having a first curvature 60 to match a curvature of the substantially flexible eyewear frame 12 when not deformed by external forces, and a second curvature 62 to match a curvature of one of the lenses 34. The second curvature 62 is less curved than and is located forwardly with respect to the first curvature 60, to thereby position the lenses 34 which are releasably engaged to the respective rigid lens retainers 26, in front of the substantially flexible eyewear frame 12.

The substantially flexible eyewear frame 12 in this embodiment may be configured in any shape such as those of eyewear 10, 10a and 10b shown in FIGS. 1-5B. The permanent engagement of the rigid lens retainers 26 to the substantially flexible eyewear frame 12 in this embodiment, may be achieved by various structural arrangements such as previously described with reference to FIGS. 2A-2D.

Figure 7:
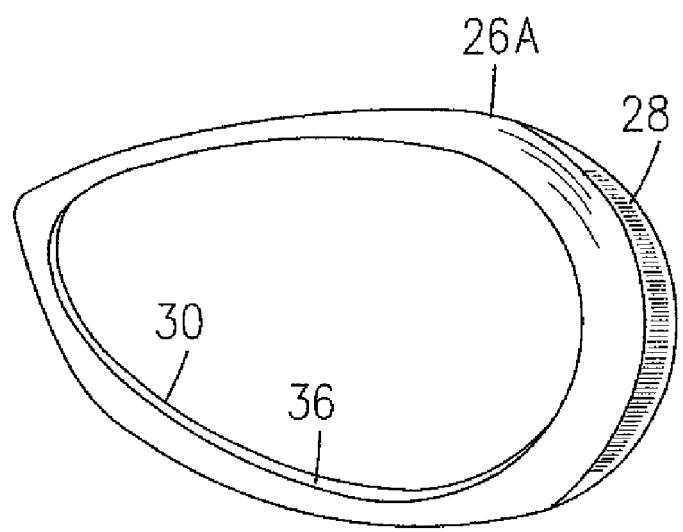
FIG. 7 is a perspective view of one of the rigid lens retainers of the eyewear shown in FIG. 6.

FIG. 7 illustrates an example of the lens retainer 26a which may be used with the substantially flexible eyewear frame 12 of eyewear 10c of FIG. 6. The rigid lens retainer 26a similar to the lens retainer 26 of eyewear 10 of FIG. 1, has a continuous circumferential outer periphery 28 and a continuous circumferential inner periphery 30. A shallow groove 36 is provided along the continuous circumferential inner periphery 30 of the rigid lens retainer 26a for releasably engaging the peripheral edge of a lens 34, as shown in FIG. 6. The lens 34 therefore covers an opening defined by the continuous circumferential inner periphery 30 of the rigid lens retainer 26a. In this embodiment, the lens 34 is relatively flat as is generally the case for prescription lenses, while the substantially flexible eyewear frame 12 is configured in a much more curved profile to fit user's head. Therefore, the rigid lens retainer 26a defines a curved profile to have the first curvature 60 at the outer periphery 28 of the rigid lens retainer 26a and to have a second curvature 62 at the inner periphery 30 of the rigid lens retainer 26a. The second curvature 62 is less curved than the first curvature 60 and the inner periphery 30 projects forwardly from the outer periphery 28 to thereby position the lens 34 which is relatively flat, in front of the eyewear frame 12 which is relatively more curved.

The above description is meant to be exemplary only and one skilled in the art will recognize that changes may be made to the embodiments described without departure from the scope of the invention disclosed. For example, the present invention may be applicable to eyewear in which the specific structural arrangements for the permanent engagement of the rigid lens retainer to the substantially flexible eyewear frame and the releasable engagement of the lens to the rigid lens retainer, are configured differently from the described embodiment. Alternative structural arrangements of the described embodiments and other modifications may be combined in various ways in order to provide a different look to the eyewear from the particular embodiments described in this application. Modifications which may be apparent to those skilled in the art, in light of a review of this disclosure, are intended to fall within the scope of the appended claims.

I claim:

1. A method of making eye glasses comprising steps in a following sequence:
    (a) providing a molding device for molding a substantially flexible glasses frame;
    (b) placing at least one rigid lens retainer in a predetermined position with respect to the molding device to permit a portion of the molding device to overlap a first portion of the rigid lens retainer;
    (c) forming the substantially flexible glasses frame with permanent engagement of the rigid lens retainer thereto in a molding process using the molding device; and then
    (d) releasably engaging at least one lens with the rigid lens retainer to have the lens be in direct contact with a second portion of the rigid lens retainer.

2. The method as claimed in claim 1 wherein the permanent engagement of the rigid lens retainer with the substantially flexible glasses frame is achieved by embedding the first portion of the rigid lens retainer in the substantially flexible glasses frame.

3. The method as claimed in claim 1 wherein the permanent engagement of the rigid lens retainer with the substantially flexible glasses frame is achieved by allowing a portion of a molding material of the substantially flexible glasses frame to flow into at least one cavity defined in the first portion of the rigid lens retainer.

4. The method as claimed in claim 1 wherein the releasable engagement of the at least one lens with the rigid lens retainer is achieved by releaseably engaging an entire peripheral edge of the at least one lens with an inner peripheral edge of a lens opening defined in the second portion of the rigid lens retainer.

5. The method as claimed in claim 1 wherein the releasable engagement of the at least one lens with the rigid lens retainer is achieved by releaseably engaging at least one engaging element projecting from the rigid lens retainer, in a cavity defined in the at least one lens.

6. The method as claimed in claim 1 further comprising forming the rigid lens retainer with the first portion having a first curvature for mating with the substantially flexible glasses frame, and a second curvature for mating with the at least one lens.

7. The method as claimed in claim 6 wherein the second curvature is less curved that the first curvature.

8. Eye glasses comprising:
    a substantially flexible molded glasses frame;
    a rigid lens retaining apparatus including first and second portions thereof, the first portion being permanently engaged with a portion of the substantially flexible molded glasses frame during a molding formation of the frame with the presence of the rigid lens retaining apparatus; and at least one lens in direct contact and releaseably engaged with the second portion of the rigid lens retaining apparatus.

9. The eye glasses as claimed in claim 8 wherein the first portion of the rigid lens retaining apparatus is embedded in the substantially flexible molded glasses frame.

10. The eye glasses as claimed in claim 8 wherein a portion of material of the substantially flexible molded glasses frame is filled into at least one cavity defined in the first portion of the rigid lens retaining apparatus.

11. The eye glasses as defined in claim 8 wherein the substantially flexible molded glasses frame comprises a pair of lens support sections, the rigid lens retaining apparatus including a pair of rigid lens retainers permanently engaged with the respective lens support sections, the at least one lens together with another lens forming a pair of lenses releasably engaged with the respective rigid lens retainers.

12. The eye glasses as defined in claim 11 wherein the rigid lens retainers encircle the respective lens and each of the rigid lens retainers comprises a circumferential outer periphery forming the first portion of the rigid lens retaining apparatus and a circumferential inner periphery defining the second portion of the rigid lens retaining apparatus.

13. The eye glasses as defined in claim 12 wherein each of the rigid lens retainers defines a curved profile having a first curvature at the outer periphery of the lens retainer and a second curvature at the inner periphery, the second curvature being less curved than the first curvature and the inner periphery projecting forwardly from the outer periphery to position the lenses having the second curvature in front of the glasses frame having the first curvature.

14. The eye glasses as defined in claim 11 wherein each of the rigid lens retainers defines a curved profile having a first curvature to match a curvature of the substantially flexible glasses frame and a second curvature to match a curvature of one of the lenses, the second curvature being less curved than and located forwardly with respect to the first curvature, to thereby position the lenses in front of the glasses frame.

15. The eye glasses as defined in claim 11 wherein the rigid lens retaining apparatus further comprises a connection portion interconnecting the pair of rigid lens retainers, the connection portion being embedded in the substantially flexible glasses frame.

* * * * *